United States Patent [19]
Sakurai

[11] Patent Number: 6,004,336
[45] Date of Patent: Dec. 21, 1999

[54] ANGIOSTOMY APPARATUS USING ULTRASONIC ENERGY AND ANGIOSTOMY METHOD

[75] Inventor: Tomohisa Sakurai, Sagamihara, Japan

[73] Assignee: Olympus Optical Co., Ltd., Tokyo, Japan

[21] Appl. No.: 09/164,718

[22] Filed: Oct. 1, 1998

[30] Foreign Application Priority Data

Oct. 6, 1997 [JP] Japan ................................. 9-272717

[51] Int. Cl.⁶ ................................................ A61B 17/32
[52] U.S. Cl. ........................................ 606/169; 227/179.1
[58] Field of Search .................................. 606/169, 151, 606/171; 604/22; 227/179.1

[56] References Cited

U.S. PATENT DOCUMENTS

| | | |
|---|---|---|
| 3,636,943 | 1/1972 | Balamuth . |
| 3,862,630 | 1/1975 | Balamuth . |
| 3,898,992 | 8/1975 | Balamuth . |
| 5,309,927 | 5/1994 | Welch ................................... 128/898 |
| 5,445,644 | 8/1995 | Pietrafitta et al. ................... 227/179.1 |
| 5,873,873 | 2/1999 | Smith et al. ............................ 606/169 |
| 5,881,943 | 3/1999 | Heck et al. .......................... 227/179.1 |

FOREIGN PATENT DOCUMENTS

WO 95/35065  12/1995  WIPO .

Primary Examiner—Michael Buiz
Assistant Examiner—Kevin Truong
Attorney, Agent, or Firm—Frishauf, Holtz, Goodman, Langer & Chick, P.C.

[57] ABSTRACT

An angiostomy apparatus has an ultrasonic oscillator for generating predetermined ultrasonic energy. A holding member has at least a substantially annular end face or an annular portion, and holds a blood vessel at its inner peripheral side. A probe is used to hold a portion of the blood vessel between itself and an outer peripheral side portion of the substantially annular end face or the annular portion of the holding member. An oscillation transmitting section transmits ultrasonic oscillation from the ultrasonic oscillator to that portion of the blood vessel which is in contact with the holding member or the probe. The holding member is a cylindrical member having a slit formed therein.

4 Claims, 3 Drawing Sheets

FIG. 2C  ULTRASONIC ANSTOMOSIS

6,004,336

ANGIOSTOMY APPARATUS USING ULTRASONIC ENERGY AND ANGIOSTOMY METHOD

BACKGROUND OF THE INVENTION

This invention relates to an angiostomy apparatus and an angiostomy method.

Conventional angiostomy operations are performed by suturing blood vessels using a needle and a thread. In addition, in light of the fact that a considerable skill is required to suture blood vessels in this way, automatic angiostomy apparatuses have come to be used for performing the angiostomy operations. Since, however, a mechanical structure for suturing thick blood vessels such as coronary arteries is hard to realize, angiostomy operations using energy are now proposed.

For example, there is a method for suturing fine blood vessels by radiating a laser beam. In this method, though, it is very difficult to bring the intimae of ends of blood vessels into tight contact with each other, and to reliably apply a laser beam onto the contact portion. Therefore, a method for accurately fixing the blood vessels and the laser beam is necessary.

Ultrasonic energy is considered another kind of suitable energy. An ultrasonic knife is considered a ultrasonic energy applied device in the medical field, in which a treatment for incising, excising or coagulating a caught organic tissue is made using ultrasonic energy. In the other industrial fields, ultrasonic energy is applied to an ultrasonic bonding apparatus or a plastic welder.

As described above, ultrasonic energy has been used in the medical field, but application of the energy to angiostomy operations has not been considered, and nor has a method for realizing the application been proposed.

BRIEF SUMMARY OF THE INVENTION

The invention has been developed under the above circumstances, and is aimed at providing an angiostomy method for applying ultrasonic energy to angiostomy operations, and an angiostomy apparatus capable of performing short-time and reliable angiostomy even in a narrow space without an excellent skill.

According to an aspect of the invention, there is provided an angiostomy apparatus comprising:

a holding member having at least a substantially annular end face or an annular portion, the holding member holding a blood vessel at an inner peripheral side thereof;

a probe for holding a portion of the blood vessel between itself and an outer peripheral side portion of the substantially annular end face or the annular portion of the holding member;

an ultrasonic oscillator; and an oscillation transmitting section for transmitting ultrasonic oscillation from the ultrasonic oscillator to that portion of the blood vessel which is in contact with the holding member or the probe.

According to another aspect of the invention, there is provided an angiostomy method comprising the steps of:

inserting a blood vessel to be anastomosed, through a slit portion formed in a holding member, into the holding member which has at least a substantially annular end face or an annular portion and the slit portion, then turning back the blood vessel on itself at one end thereof to expose an intima thereof;

forming an incised portion of a blood vessel into which the first-mentioned blood vessel is inserted, inserting the turned-back end portion of the first-mentioned blood vessel into the incised portion to thereby bringing the intimae of the blood vessels into contact with each other;

holding those portions of the blood vessels which are to be anastomosed between a probe and an outer peripheral portion of the substantially annular end face or the annular portion of the holding member; and transmitting ultrasonic oscillation from an ultrasonic oscillator to that portion of the holding member or the probe, which is in contact with portions of the vessels, to thereby apply oscillation to contact portions of the vessels in order to anastomose them.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 2A–2D are views, useful in explaining the procedure of angiostomy; and

DETAILED DESCRIPTION OF THE INVENTION

The embodiments of the invention will be described in detail with reference to the accompanying drawings.

Figures 1A, 1B:
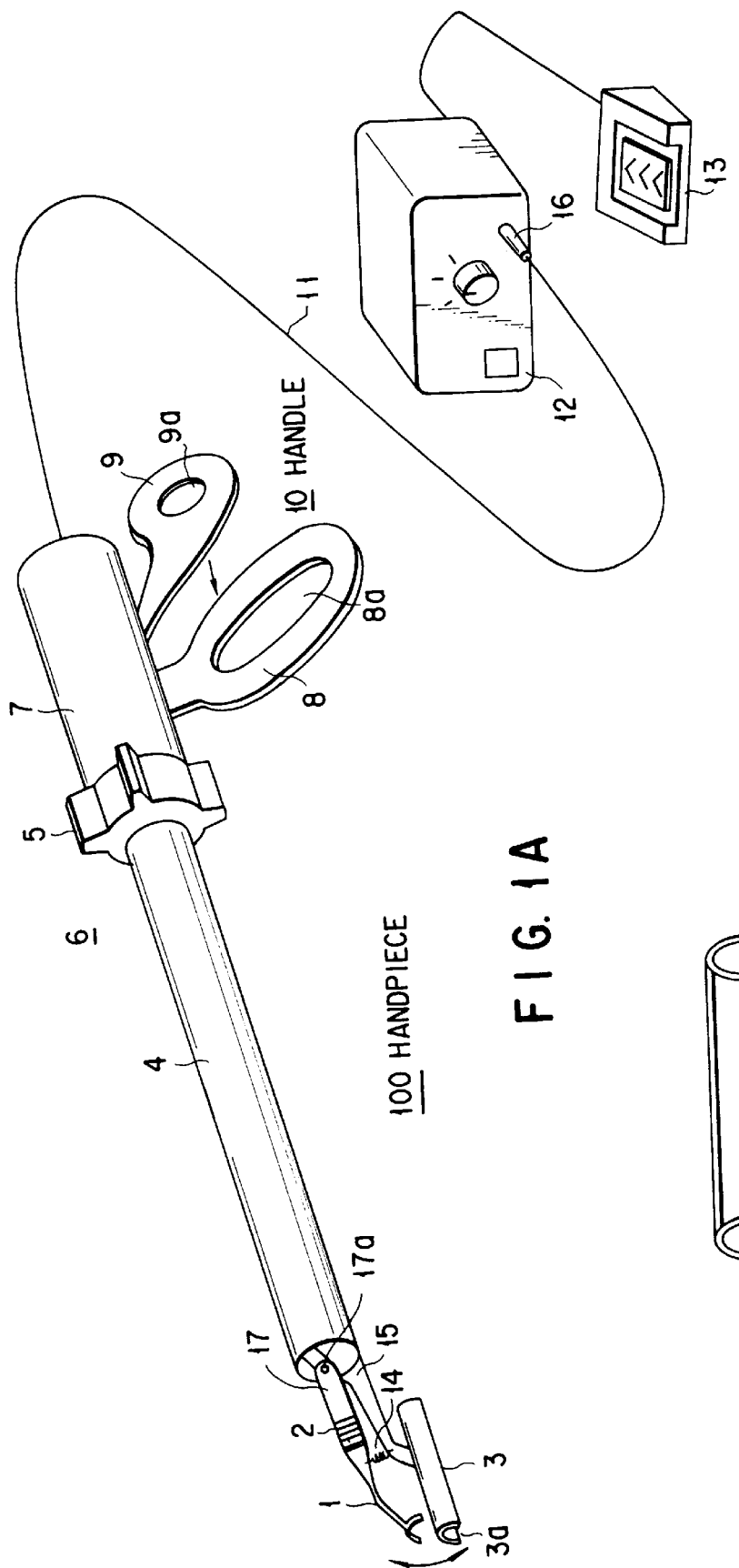
FIGS. 1A and 1B are views, showing an angiostomy system to which an angiostomy apparatus according to a first embodiment of the invention is applied.

FIG. 1A is a perspective view, showing an angiostomy system to which an angiostomy apparatus according to a first embodiment of the invention is applied. As is shown in the figure, the system includes a slim cylindrical sheath 4, and a cylindrical grip sheath 7 provided on the proximal end of the sheath 4. The sheathes 4 and 7 constitute the main body 6 of a hand piece 100. Reference numeral 5 denotes a rotary operation knob.

The grip sheath 7 is provided with a handle 10 having a stationary handle 8 and a movable handle 9. Finger insertion ring sections 8a and 9a are provided in the handles 8 and 9, respectively. The handle 10 is coupled to one end of an operation rod (not shown) accommodated in the hand piece main body 6. The other end of the operation rod is coupled to a coupling section 17 located outside the hand piece main body 6, and also to a probe 1 having a semicircular end, with an ultrasonic oscillator 2 interposed therebetween. The coupling section 17, the ultrasonic oscillator 2 and the probe 1 constitute an ultrasonic treatment section which can pivot vertically (in directions indicated by the arrows) on the fulcrum 17a of the coupling section 17. Further, a blood vessel holding member 3 is fixed to the lower tip of the sheath 4. The blood vessel holding member 3 is formed of a cylindrical member of a heat-resistive resin such as teflon, and has a slit 3a formed in the lower side surface of the member 3 and extending along its length. The blood vessel holding member 3 is not limited to the cylindrical one, but may have other shapes. It suffices if the member 3 has a substantially annular end face or an annular portion to be fitted in the semicircular end of the probe 1. For example, a member consisting of two rings and a bar which couples the rings, as shown in FIG. 1B, may be used. Moreover, the member 3 can be detachable from the hand piece main body 6, together with a support section 15. The probe 1 and the support section 15 are coupled to each other by means of a spring 14 as an urging member.

The hand piece main body 6 has a passage formed therein for electrically connecting the ultrasonic oscillator 2 and a power supply cord 11. The power supply cord 11 is connected to a terminal 16 of a power supply (not shown) installed in an ultrasonic driving unit main body 12 for driving the ultrasonic oscillator. A foot switch 13 is connected to the ultrasonic driving unit main body 12.

Referring to FIGS. 1A, 1B and 2A–2D, the procedure of angiostomy, i.e. in this case, the anastomosing of the internal thoracic artery and coronary artery, will be described.

Figure 2A:
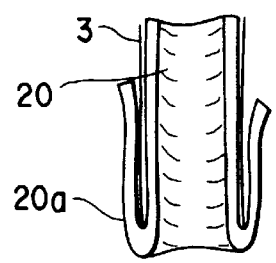

First, as is shown in FIG. 2A, an internal thoracic artery 20 to be anastomosed is inserted into the blood vessel holding member 3 through the slit 3a of the member 3, the artery is turned back on itself at one end to thereby expose a blood vessel intima surface 20a.

Figure 2B:
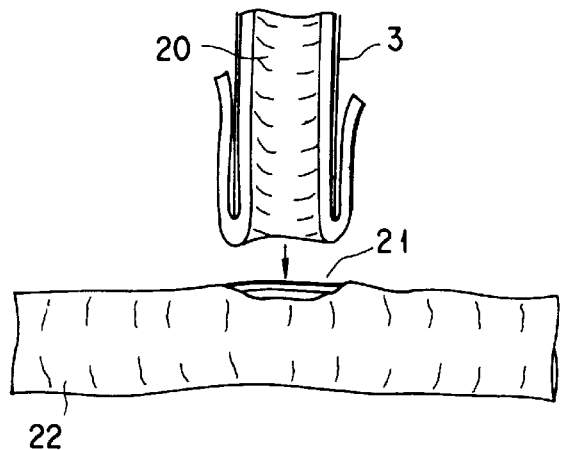

Referring then to FIG. 2B, an incised portion 21 is formed in the coronary artery into which the artery 20 is anastomosed, and the turned-back artery 20 is inserted into the incised portion 21 to a sufficient degree, thereby slightly pulling back the artery 20 and bringing the inner surfaces of the coronary artery 22 and the artery 20 into contact with each other.

If, in this state, the operator rotates the handle 10 in the direction indicated by the arrow in FIG. 1, the ultrasonic treatment section including the probe 1 rotates in a closing direction with respect to the blood vessel holding member 3. After the handle 10 is rotated to some extent, the probe 1 is urged and fixed against the blood vessel holding member 3 by the urging force of the spring 14, with the internal thoracic artery 20 and the coronary artery 22 held therebetween, as is shown in FIG. 2C.

If in this state, the operator operates the foot switch 13 to turn on the power, electric energy is supplied to the ultrasonic oscillator 2 to start ultrasonic oscillation. Linked with the ultrasonic oscillation, the probe 1 oscillates, thereby applying that oscillation to the contact portion of the internal thoracic artery 20 and the coronary artery 22, which is parallel to the contact surface (the vertical direction in FIG. 2C). Thus, anastomosis is performed. Then, the direction in which the oscillation is applied is changed to thereby perform anastomosis. As a result, the anastomosis all over the periphery is completed.

The oscillation of the ultrasonic oscillator 2 by turning on the power supply may be linked with the pivoting of the handle 10.

Figure 2D:
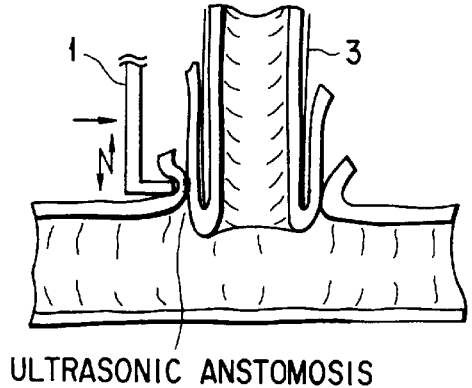
Figure 2D:
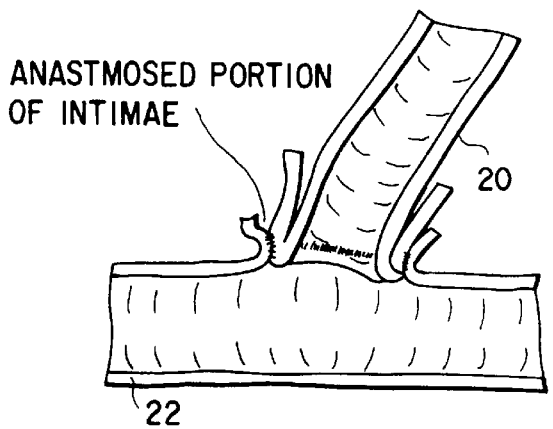

Lastly, the internal thoracic artery 20 inserted in the coronary artery 22 is pulled out, which is the termination of the angiostomy (FIG. 2D).

Although in the above embodiment, the probe 1 is urged against the blood vessel holding member 3 by the urging force of the spring 14 as the urging member, the urging member is not always necessary. It may be modified such that the probe 1 is urged against the blood vessel holding member 3 simply by the handle operation of the operator.

Figure 3:
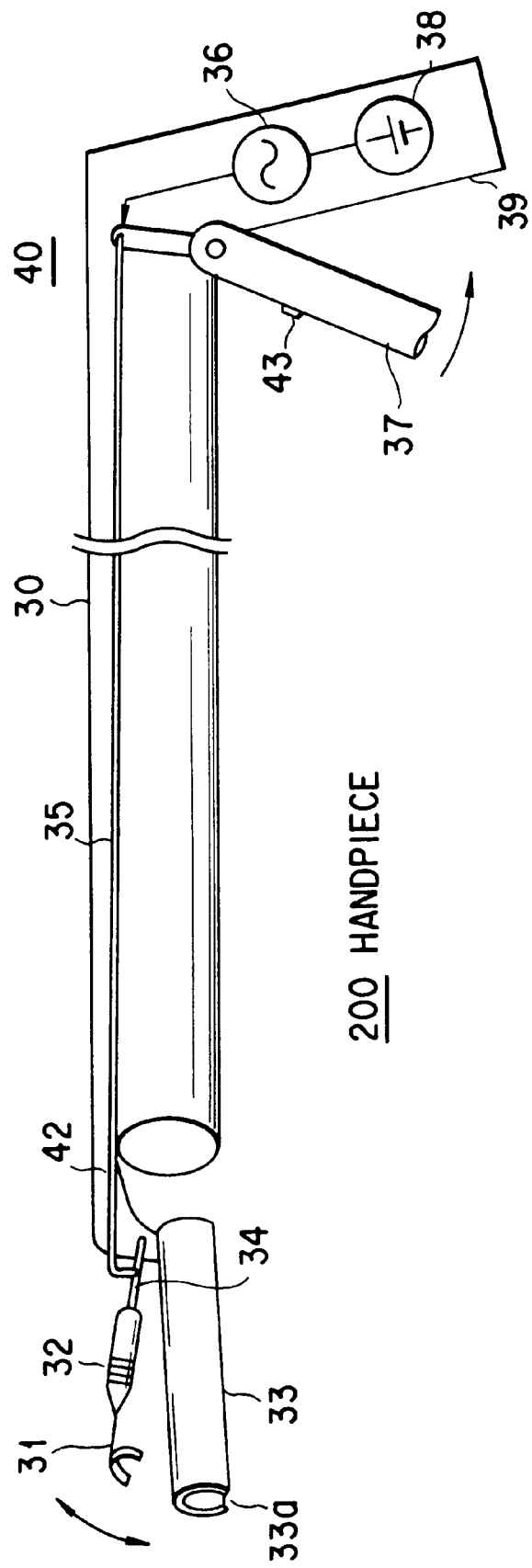
FIG. 3 is a perspective view, showing an angiostomy system to which an angiostomy apparatus according to a second embodiment of the invention is applied.

FIG. 3 shows an angiostomy system to which an angiostomy apparatus according to a second embodiment of the invention is applied. In the second embodiment, a hand piece 200 has a main body 40 of a gun shape, which consists of a slim cylindrical sheath 30 and a handle section 39 formed integral with the sheath 30 as one body. The handle section 39 contains a generator 36 and a power supply 38 such as a battery. Since this makes it unnecessary to extend the power supply cord to the outside of the main body 40, it is easy for the operator to perform operations. Further, a switch 43 is provided in the handle section 39 for starting high frequency oscillation.

An operating section 37 is provided at the proximal end of the sheath 30, and a support section 42 is formed integral with the frond end of the sheath 30, thereby supporting a blood vessel holding member 33.

The operating section 37 is coupled with an operating rod 35 in the sheath 30. The operating rod 35 extends through the sheath 30 and is coupled with an ultrasonic oscillator 32 by a coupling section 34. The ultrasonic oscillator 32 is coupled with a probe 31 with a semicircular end. The sheath 30 has a passage formed therein from the generator 36 and the ultrasonic oscillator 32 for transmitting electric energy. The probe 31 and the ultrasonic oscillator 32 constitute an ultrasonic treatment section.

The above-described structure can perform angiostomy in the same procedure as employed in the first embodiment. Therefore, only a simple description will be given thereof. When the operator has rotated the operating section 37 in a direction indicated by the arrow in FIG. 3, the ultrasonic treatment section rotates to thereby urge the probe 31 against the blood vessel holding member 33, with the internal artery 20 and the coronary artery 22 held therebetween.

When in this state, the switch 43 provided on the handle section 39 has been pushed, the generator 36 is driven thereby to supply electric energy to the ultrasonic oscillator 32 and start ultrasonic oscillation. Linked with the ultrasonic oscillation by the oscillator 32, the probe 31 performs ultrasonic oscillation, whereby the internal thoracic artery 20 and the coronary artery 22 are oscillated and anastomosed.

Oscillation of the ultrasonic oscillator 32 by driving the generator 36 may be linked with pivoting of the operating section 37 performed by the operator. Moreover, it may be modified such that the generator 36 is automatically driven when the operating section 37 has reached a predetermined position after being operated by the operator.

Although in the above-described embodiments, the blood vessel holding members have respective slits formed therein, these slits can be omitted if a blood vessel is inserted into each blood vessel holding member through an opening formed in an end thereof. In this case, the member can be formed of ceramic or a metallic material as well as the heat-resistive resin.

In addition, although in the above embodiments, the ultrasonic oscillator is provided on the probe side, it may be provided on the blood vessel holding member side.

As described above, the invention provides a specific method for applying ultrasonic energy to angiostomy operations, which enables performance of short-time and reliable angiostomy even in a narrow space without an excellent skill.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

I claim:

1. An angiostomy apparatus comprising:

a holding member having at least a substantially annular end face or an annular portion, the holding member holding a blood vessel at an inner peripheral side thereof;

a probe for holding a portion of the blood vessel between itself and an outer peripheral side portion of the substantially annular end face or the annular portion of the holding member;

an ultrasonic oscillator; and an oscillation transmitting section for transmitting ultrasonic oscillation from the ultrasonic oscillator to that portion of the blood vessel which is in contact with the holding member or the probe.

2. An angiostomy apparatus according to claim 1, wherein the holding member is a cylindrical member having a slit formed therein.

3. An angiostomy apparatus according to claim 1, further comprising an urging member for urging the probe against the holding member.

4. An angiostomy method comprising the steps of:

inserting a blood vessel to be anastomosed, through a slit portion formed in a holding member, into the holding member which has at least a substantially annular end face or an annular portion and the slit portion, then turning back the blood vessel on itself at one end thereof to expose an intima thereof;

forming an incised portion of a blood vessel into which the first-mentioned blood vessel is inserted, inserting the turned-back end portion of the first-mentioned blood vessel into the incised portion to thereby bringing the intimae of the blood vessels into contact with each other;

holding those portions of the blood vessels which are to be anastomosed between a probe and an outer peripheral portion of the substantially annular end face or the annular portion of the holding member; and transmitting ultrasonic oscillation from an ultrasonic oscillator to that portion of the holding member or the probe, which is in contact with portions of the vessels, to thereby apply oscillation to contact portions of the vessels in order to anastomose them.

* * * * *